United States Patent [19]

Foguet et al.

[11] Patent Number: 5,395,841
[45] Date of Patent: Mar. 7, 1995

[54] 4-BENZYLPIPERIDINES FOR TREATING PHYCHOSIS

[75] Inventors: Rafael Foguet; Jordi Bolós; Aurelio Sacristán; José A. Ortiz, all of Barcelona, Spain

[73] Assignee: Ferrer Internacional, S.A., Barcelona, Spain

[21] Appl. No.: 71,265

[22] Filed: Jun. 4, 1993

[30] Foreign Application Priority Data

Jun. 4, 1992 [ES] Spain .................................... 9201158
May 3, 1993 [ES] Spain .................................... 9300928

[51] Int. Cl.⁶ .................... A61K 31/445; C07D 211/18
[52] U.S. Cl. .................................... 514/317; 546/16; 546/236; 546/237
[58] Field of Search .................... 546/16, 237, 236; 514/317

[56] References Cited

U.S. PATENT DOCUMENTS

| | | | |
|---|---|---|---|
| 4,588,728 | 5/1986 | Ferris | 514/255 |
| 4,690,931 | 9/1987 | Wick | 514/317 |
| 4,709,094 | 11/1987 | Weber et al. | 514/634 |
| 4,929,734 | 5/1990 | Coughonour et al. | 546/338 |
| 5,061,728 | 10/1991 | Koe | 514/520 |

FOREIGN PATENT DOCUMENTS

| | | |
|---|---|---|
| 0261688 | 3/1988 | European Pat. Off. . |
| 0372776 | 6/1990 | European Pat. Off. . |
| 7431 | 2/1970 | France . |
| 2681319 | 9/1991 | France . |
| 93/00313 | 1/1993 | WIPO . |

OTHER PUBLICATIONS

Clark et al "Principle of Psychopharmacology" Academic Press, pp. 166–167 (1970).

Largent et al. (1988) European Journal of Pharmacology 155:345–347.

Deutsch et al. (1988) Clinical Neuropharmacology, vol. 11 (2):105–119.

Berge et al. (1977) Journal of Pharmaceutical Sciences, (66(1)):1–19.

J. B. Lassen, European Journal of Pharmacology, 36 (1976), pp. 385–393.

B. Costall, et al., European Journal of Pharmacology, 50 (1978), pp. 39–50.

P. J. Gilligan, et al., J. Med. Chem., 35 (1992), pp. 4344–4361.

M. Williams, Annual Reports in Medicinal Chemistry, 27 (1992), pp. 1–10.

J. P. Yevich, et al., J. Med. Chem., 35 (1992), pp. 4516–1525.

Primary Examiner—Celia Chang
Attorney, Agent, or Firm—Birch, Stewart, Kolasch & Birch

[57] ABSTRACT

4-Benzylpiperidine derivatives of the formula:

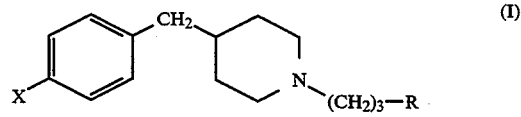

(I)

or a pharmaceutically acceptable acid addition salt thereof, wherein X is hydrogen or fluorine and R is hydrogen, or a group selected from p-fluorobenzoyl, α-hydroxy-p-fluorobenzyl, p-fluorophenoxy, bis(p-fluorophenyl)methyl and 8-azaspiro[4,5]decane-7,9-dione-8-yl-methyl, with the proviso that X and R may not be simultaneously hydrogen and p-fluorobenzoyl respectively.

Such compounds are useful as sigma-receptor ligands.

10 Claims, No Drawings

4-BENZYLPIPERIDINES FOR TREATING PHYCHOSIS

BACKGROUND OF THE INVENTION

The present invention relates to novel and therapeutically valuable 4-benzylpiperidines, their pharmaceutically acceptable acid addition salts, a process for their preparation, and their use as sigma-receptor ligands.

U.S. Pat. No. 4,588,728 describes the treatment of psychosis with cis-9[3-(3,5-dimethylpiperazinyl)-propyl]carbazol. U.S. Pat. No. 4,709,094 discloses 1,3-disubstituted guanidines as well as their utility in the diagnosis and treatment of hallucinations associated with psychotic disorders and chronic mental depression. U.S. Pat. No. 4,929,734 discloses N-substituted 1-(1,2,3,6-tetrahydro-3-pyridinyl)oximes and N-substituted 1-(1,2,3,6-tetrahydro-4-pyridinyl)oximes and their utility in the treatment of depression, psychoses and/or inflammatory diseases. U.S. Pat. No. 5,061,728 describes the utility of 4-phenyl-1,2,3,4-tetrahydro-1-naphthalenamine derivatives in the treatment of psychoses, inflammations and their use as immunosuppressants. The compounds claimed in all these patents have a shared affinity as sigma-receptor ligands to the Central Nervous System. To this effect, literature reviews by B. L. Largent et al (Eur. J. Pharmacol. 155, 345–7, 1988) and S. I. Deutsch et al 1988) and S. I. Deutsch et al (Clinical Neuropharmacology, 11(2), 105–119, 1988) are illustrative of the biochemical, pharmacological and clinical aspects of sigma-receptor ligands.

SUMMARY OF THE INVENTION

The present inventors have found that novel 4-benzylpiperidines and pharmaceutically acceptable acid addition salts thereof exhibit an outstanding activity as sigma-receptor ligands.

DETAILED DESCRIPTION OF THE INVENTION

The 4-benzylpiperidines of the present invention are represented by the following formula (I):

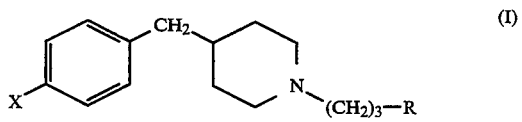

In the above formula, X is hydrogen or fluorine and R is hydrogen, or a group selected from p-fluorobenzoyl, α-hydroxy-p-fluorobenzyl, p-fluorophenoxy, bis(p-fluorophenyl)methyl and 8-azaspiro[4,5] decane-7,9-dione-8-yl-methyl, with the proviso that X and R may not be simultaneously hydrogen and p-fluorobenzoyl respectively. The compounds of formula (I) are prepared according to the following scheme:

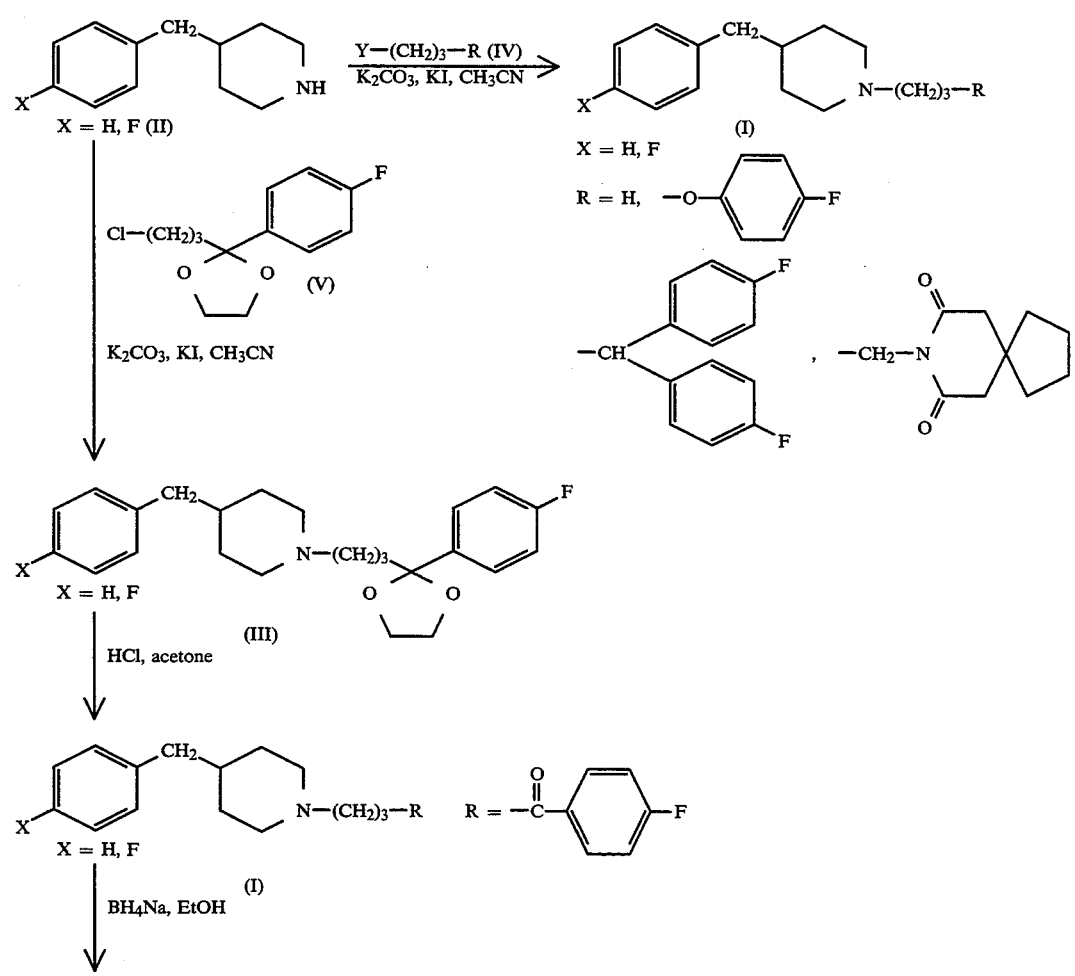

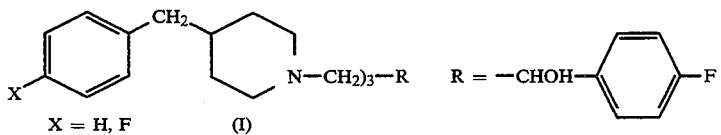

X = H, F  (I)

In accordance with the above scheme, 4-benzylpiperidines (II) are alkylated either with 3-halopropyl derivatives of the general formula (IV), wherein Y is a halogen selected from chlorine, bromine or iodine and R is hydrogen, p-fluorophenoxy, bis(p-fluorophenyl)methyl or 8-azaspiro[4,5]decane-7,9-dione-8-yl-methyl, or with 2-(3-chloropropyl)-2-(p-fluorophenyl)-1,3-dioxolane (V) in the presence of a carbonate or alkaline acid carbonate or alkaline earth carbonate, preferably potassium carbonate, and in a nonpolar medium such as acetonitrile. End products, wherein R is as defined for (IV), or the ethylene ketal intermediates of the general formula (III) are thus obtained. Hydrolysis of the latter compounds in an acid medium, such as hydrochloric acid in acetone, yields end products wherein R is p-fluorobenzoyl. In turn, reduction of these end products with sodium borohydride in ethanol or other conventional arylketone reductor leads to the end products wherein R is α-hydroxy-p-fluorobenzyl; X represents hydrogen or fluorine throughout the scheme.

Pharmaceutically acceptable acid addition salts of the compounds of formula (I) include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate. caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluensulfonate, phenylacetate, citrate, lactate, tartrate, methansulfonate, and the like. Also contemplated are salts of amino acids such as arginate and the like and gluconate, galacturonate (see, for example, Berge, S. M. et al, "Pharmaceutical Salts" Journal of Pharmaceutical Science, Vol. 66, pages 1–19, 1977).

Applicants have found out that the compounds of the present invention, although they are chemically quite different from those of the above prior art patents, possess an important affinity as sigma-receptor ligands. Due to such activity, they are potentially useful in the treatment of some sigma receptor-related mental disorders, mainly psychosis and schizophrenia.

Sigma-receptor binding has been determined according to the following experimental method:

2 nM solution of 3-PPP radioactive $((+)[^3H]$3-[3-hydroxyphenyl]-N-(1-propyl)-piperidine), which acts as a specific ligand, is incubated for 90 min at 25° C. with the membrane corresponding to 40 mg of guinea pig total brain, and then buffered to pH 8.5 with TRIS.HCl. Thus, total binding of ligand to membranes is attained. The nonspecific binding is determined by adding a micromolar concentration of unlabelled 3-PPP. From inhibition rate of the nonspecific binding obtained by adding eleven different concentrations of the compounds to be tested, $IC_{50}$ values (inhibitory concentration 50%) are calculated. After incubation, the samples are filtered using a glass fiber filter and then washed three times with TRIS.HCl buffer. Receptor-bound radioactivity is retained on the membrane and measured by liquid scintillation. Results presented in Table 1 are expressed as $IC_{50}$ (nM).

TABLE 1

| Compound | $IC_{50}$ (nM) |
| --- | --- |
| Example 1 | 2.95 |
| Example 5 | 2.40 |
| Example 6 | 1.49 |
| Example 7 | 8.80 |
| Example 8 | 4.50 |
| Example 9 | 72.0 |
| Example 10 | 1.89 |
| Example 11 | 4.20 |

The data from Table 1 suggest that the compounds of the present invention are extremely potent and may be useful in the treatment of some Central Nervous System diseases subjected to the function of sigma receptors. The compounds can specially be used in anoxia, anxiety, convulsions, schizophrenia, hypoxia, cerebral ischemia, psychosis and stress. The compounds mixed with suitable solvents may be administered by oral or rectal route or by injection at daily doses ranging from 0.5 to 100 mg, and most preferably from 1 to 30 mg.

A number of examples will now be described in non-limitative manner to illustrate the invention.

EXAMPLE 1

4-p-Fluorobenzyl-1-propylpiperidine hydrochloride

A mixture of 4-(p-fluorobenzyl)piperidine (5 g, 26 mmol), propyl iodide (4.4 g, 26 mmol) and potassium carbonate (2 g, 15 mmol) in acetonitrile (30 ml) is heated under reflux for 16 hours, then filtered and the filtrate is evaporated to dryness. The residue is treated with saturated $CO_3HNa$ solution and extracted with chloroform. Evaporation of chloroform extracts gives an oil which is dissolved in acetone, added HCl ethereal solution and precipitated by addition of $Et_2O$. The resulting precipitate is purified by recrystallization from acetone-ether to give 2 g (28%) of a solid. mp: 201°–203° C.

Elemental analysis for $C_{15}H_{22}NF.HCl$ (%): (calculated) C 66.28 H 8.53 N 5.15; (found) C 66.12 H 8.62 N 5.45.

IR $(cm^{-1})$: 2400–2900, 1620, 1510, 1250, 1230.

NMR $(CD_3OD)$: 0.97 (t, J=7Hz, 3H, $CH_3$), 1.4–2.0 (m, 7H, 3-H, 4-H, 5-H, $CH_2CH_3$), 2.45–2.65 (m, 2H, $PhCH_2$), 2.65–3.2 (m, 4H, 2-$H_{ax}$, 6-$H_{ax}$, N—CH$_2$—$C_2H_5$), 3.55 (d a, J=12Hz, 2H, 2-$H_{eq}$ and 6-$H_{eq}$), 6.97 (t, J=9Hz, 2H, Ph-3H and -5H), 7.20 (dd, J=9 and 6Hz, 2H, Ph-2H and 6H).

EXAMPLE 2

4-Benzyl-1-(4-p-fluorophenyl-4,4-ethylendioxy)butyl-piperidine

A mixture of 4-benzylpiperidine (10 g, 57 mmol), 2-(3-chloro-propyl)-2-(p-fluorophenyl))1,3-dioxolane (14 g, 57 mmol), potassium carbonate (5 g, 36 mmol) and potassium iodide (0.5 g, 3 mmol) in acetonitrile (50 ml) is heated under reflux for 16 hours. The resulting solution is allowed to cool and filtered, and the residue is washed with acetonitrile. The filtrates are evaporated to give 20 g (91%) of an oil, which is used in the next step without additional purification.

IR (cm$^{-1}$): 1600, 1500, 1450, 1220, 1040.

NMR (CDCl$_3$): 1.2–2.0 (m, 11H, 3-H, 4-H, 5-H, 2-H$_{ax}$, 6-H$_{ax}$, Bu-2H and Bu-3H), 2.27 (t, J=7Hz, 2H, Bu-1H), 2.52 (d, J=4Hz, 2H, PhCH$_2$), 2.85 (da, J=11Hz, 2H, 2-H$_{eq}$ and 6-H$_{eq}$), 3.6–4.1 (m, 4H, OCH$_2$CH$_2$O), 6.97 (t, J=8Hz, 2H, FPh-3H and -5H), 7.1–7.2 (m, 5H, Ph—H), 7.4 (dd, J=8 and 5Hz, 2H, FPh-2H and -6H).

EXAMPLE 3:

4-Benzyl-1-(4-p-fluorophenyl-4-oxo)butylpiperidine hydrochloride

A solution of the ketal (19 g, 49.5 mmol) obtained in the preceding step in acetone (40 ml) and 3N HCl (40 ml) is heated to 60° C. for 1 hour. The resulting solution is concentrated in vacuo, basified with a solution of 3N NaOH and extracted with ethyl acetate. The extracts are evaporated, dried over sodium sulfate giving 16 g (95%) of an oil which solidifies slowly. The title compound is purified by the formation of hydrochloride and crystallizes from EtOH:Et$_2$O (1:3) as a solid. mp: 181°–184° C.

Elemental analysis for C$_{22}$H$_{26}$NOF.HCl (%): (calculated) C 70.29 H 7.24 N 3.73 Cl 9.43; (found) C 70.24 H 7.42 N 3.56 Cl 9.13.

IR (KBr) cm$^{-1}$: 2300–2800, 1680, 1600.

NMR (CD$_3$OD): 1.5–2.4 (m, 9H, 3-H, 4-H, 5-H, 2-H$_{ax}$, 6-H$_{ax}$ and Bu-2H), 2.65 (d, J=6Hz, 2H, PhCH$_2$), 3.0 (ta, J=11HZ, 2H, 2-H$_{ax}$ and 6-H$_{ax}$), 3.2 (t, J=7Hz, 2H, Bu-1H), 3.65 (da, J=11HZ, 2H, 2-H$_{eq}$ and 6-H), 7.1–7.3 (m, 7H, FPH-3H and -5H, and Ph—H), 8.05 (dd, J=8 and 6Hz, 2H, FPh-2H and -6H).

EXAMPLE 4

4-p-Fluorobenzyl-1-(4,4-ethylendioxi-4-p-fluorophenyl)butyl-piperidine

From 4-p-fluorobenzylpiperidine (5,3 g, 27 mmol), 2-(3-chloropropyl)-2-(p-fluorophenyl)-1,3-dioxolane (6.6 g, 27 mmol), potassium carbonate (3 g, 22 mmol) and potassium iodide (0.3 g, 1.8 mmol) and operating as described in Ex. 3, an oil is obtained which is purified by silica gel column chromatography (eluent: MeOH-AcOEt, 1:9) giving 4.73 g (44%).

IR (film) cm$^{-1}$: 1610, 1510, 1230, 1050, 850.

NMR (CDCl$_3$): 1.2–2.0(m, 11H, 3-H, 4-H, 5-H, 2-H$_{ax}$, 6-H$_{ax}$, Bu-2H, and Bu-3H), 2.25 (t, J=7Hz, 2H, Bu-1H), 2.85, (d, J=4Hz, 2H, PhCH$_2$), 2.85 (da, J=11Hz, 2H, 2-H$_{eq}$ and 6-H$_{eq}$), 3.6–4.1 (m, 4H, OCH$_2$CH$_2$O), 6.8–7.2 (m, 6H, benzoyl-3H and -5H, and benzyl-H), 7.4 (dd, J=8 and 6Hz, 2H, benzoyl-2H and -6H).

EXAMPLE 5

4-p-Fluorobenzyl-1-(4-p-fluorophenyl-4-oxo)butyl-piperidine hydrochloride

A solution of the ketal (4.73 g, 12 mmol) obtained in Ex. 4 in acetone (50 ml) and 20% HCl (50 ml) is heated to 60° C. for 90 min, concentrated in vacuo till removal of the acetone, basified with 3N NaOH and extracted with chloroform. Evaporating the extracts give 4.2 g (98%) which are dissolved in ether and precipitated by addition of HCl ethereal solution. The precipitate recrystallizes from isopropanol giving 2.47 g of a solid. mp: 170°–172° C.

Elemental analysis for C$_{22}$H$_{25}$NOF$_2$.HCl (%): (calculated) C 67.08 H 6.65 N 3.56 Cl 9.00; (found) C 67.00 H 6.66 N 3.66 Cl 8.79.

IR (cm$^{-1}$): 2200–2800, 1690, 1600, 1510, 1220.

NMR (CD$_3$OD): 1.5–2.4 (m, 9H, 3-H, 4-H, 5-H, 2-H$_{ax}$, 6-H$_{ax}$ and Bu-2H), 2.65 (d, J=6Hz, 2H, PhCH$_2$), 3.0 (ta, J=11Hz, 2H, 2-H$_{ax}$ and 6-H$_{ax}$), 3.2 (t, J=7Hz, 2H, Bu-1H), 3.65 (da, J=11Hz, 2H, 2-H$_{eq}$ and 6-H$_{eq}$), 6.9–7.3 (m, 6H, benzoyl-3H and -5H, and benzyl-H), 8.07 (dd, J=8 and 6Hz, 2H, benzoyl-2H and -6H).

EXAMPLE 6

4-Benzyl-1-(4-hydroxi-4-p-fluorophenyl)butylpiperidine hydrochloride

To a solution of 6 g (15 mmol) of the ketone obtained in Ex. 3 in absolute ethanol (50 ml), sodium borohydride (4 g, 106 mmol) is added and stirred overnight at room temperature. After heating to boiling point and evaporating to dryness, the residue is treated with water, basified with a solution of 3N NaOH and extracted with ethyl acetate. Evaporating the extracts give an oil which is solidified slowly, then dissolved in absolute ethanol followed by addition of HCl ethanol solution to acid pH. A precipitate obtained by adding ether recrystallizes from EtOH-Et$_2$O (1:1) to give 4 g (66%). mp: 178°–183° C.

Elemental analysis for C$_{22}$H$_{28}$NOF.HCl (%): (calculated) C 69.91 H 7.74 N 3.70 Cl 9.38; (found) C 69.61 H 7.62 N 4.02 Cl 9.08.

IR (cm$^{-1}$): 3350. 2300–2800, 1620, 1510, 1230.

NMR (CD$_3$OD—D$_2$O); 1.4–2.1 (m, 11H, 3-H, 4-H, 5-H, Bu-2H, Bu-3H, 2-H$_{ax}$, 6-H$_{ax}$), 2.65 (d, J=6Hz, 2H, PhCH$_2$), 2.7–3.3 (m, 4H, 2-H$_{ax}$, 6-H$_{ax}$ and Bu-1H), 3.55 (da, J=11Hz, 2H, 2-H$_{eq}$ and 6-H$_{eq}$), 4.7 (dd, J=6 and 3Hz, 1H, CHOH), 6.9–7.5 (m, 9H, Ph—H).

EXAMPLE 7

4-(p-Fluorobenzyl)-1-(4-fluorophenyl-4-hydroxy)butyl-piperidine hydrochloride

From the ketone (3 g, 7.6 mmol) obtained in Ex. 5 and sodium borohydride (2 g, 53 mmol) and operating as described in Ex. 6, a product is obtained which, after recrystallization from EtOH-iPrOH (1:1), yields 2 g (66%) of a solid. mp: 188°–190° C.

Elemental analysis for C$_{22}$H$_{27}$NOF$_2$.HCl (%): (calculated) C 66.74 H 7.13 N 3.54 Cl 8.95; (found) C 66.43 H 6.84 N 3.60 Cl 7.69.

IR (KBr) cm$^{-1}$: 3160, 2300–3800, 1610, 1510, 1230, 850.

NMR (CD$_3$OD): 1.5–2.1 (m, 11H, 3-H, 4-H, 5-H, Bu-2H, Bu-3H), 2.65 (d, J=6Hz, 2H, PhCH$_2$), 2.7–3.2 (m, 4H, 2-H$_{ax}$, 6-H$_{ax}$, and Bu-1H), 3.55 (da, J=11Hz, 2H, 2-H$_{eq}$ and 6-H$_{eq}$), 4.7 (dd, J=6 and 3Hz, 1H, CHOH), 6.85–7.25 (m, 6H, Ph—H), 7.40 (dd, J=8 and 6HZ, 2H, Ph—H).

EXAMPLE 8

4-(p-Fluorobenzyl)-1-[3-(p-fluorophenoxy)propyl]-piperidine dibenzoate

A mixture of 4-(p-fluorobenzyl)piperidine (5 g, 26 mmol), 1-(3-chloropropyl)-4-fluorobenzene (4.9 g, 26 mmol), potassium carbonate (2.24 g, 16 mmol) and potassium iodide (0.5 g, 3 mmol) in acetonitrile (50 ml) is heated under reflux for 16 hours. The solid residue is cooled, filtered and washed with acetonitrile, and the filtrate is evaporated in vacuo yielding an oil which is dissolved in ether and precipitated by addition of an ethereal solution of benzoic acid. Recrystallization from Et$_2$O gives a white solid which corresponds to a salt with two molecules of benzoid acid. mp: 93°–95° C.

Elemental analysis for C$_{35}$H$_{37}$NO$_5$F$_2$ (%): (calculated) C 71.29 H 6.33 N 2.38; (found) C 71.28 H 6.47 N 2.56.

IR (KBr) cm$^{-1}$: 3200–3700, 2200–3000, 1800–2200, 1685, 1600, 1520, 1230, 730, 720.

NMR (CDCl$_3$): 1.6–2.0 (m, 5H, 3-H, 4-H and 5-H), 2.1–2.45 (m, 4H, Pr-2H, 2-H$_{ax}$ and 6-H$_{ax}$), 2.57 (da, J=4.5Hz, 2H, PhCH$_2$), 3.15 (dd, J=9 and 5.5Hz, 2H, Pr-1H), 3.70 (da, J=12Hz, 2H, 2-H$_{eq}$ and 6-H$_{eq}$), 4.0 (t, J=6Hz, 2H, Pr-3H), 6.7–7.2 (m, 8H, Ph—H), 7.3–7.6 (m, 3H, benzoic-3H, -4H and -5H), 8.1 (dd, J=7 and 3Hz, 2H, benzoic-2H and -6H), 12.0 (s, 2H, COOH).

EXAMPLE 9

4-(p-Fluorobenzyl)-1-[4,4-bis(p-fluorophenyl)butyl]-piperidine tribenzoate

From 4-(p-fluorobenzyl)piperidine (5 g, 26 mmol) and 4,4-bis(fluorophenyl)butyl chloride (6.03 g, 26 mmol) and operating as described in Ex. 8, an oil is obtained which is purified by silica gel column chromatography (eluent: MeOH-AcOEt, 1:9), dissolved in ether and treated with an ethereal solution of benzoic acid. By addition of hexane, a solid is precipitated which recrystallizes from ether-hexane giving a solid corresponding to a salt with three molecules of benzoic acid. mp: 67°–70° C.

Elemental analysis for C$_{49}$H$_{48}$NO$_6$F$_3$ (%): (calculated) C 73.21 H 6.02 N1.74; (found) C 73.18 H 5.85 N 19.2.

IR (cm$_{-1}$): 2000–2800, 1710, 1510, 1245, 1220, 820.

NMR (CDCl$_3$): 1.4–2.2 (m, 9H), 2.2–2.6 (m, 4H, PhCH$_2$, 2-H$_{ax}$ and 6-H$_{ax}$), 3.0 (ta, J=8Hz, 2H, Bu-1H), 3.62 (da, J=12Hz, 2H, 2-H$_{eq}$ and 6-H$_{eq}$), 3.80 (t, J=8Hz, 1H, Bu-4H), 6.7–7.2 (m, 12H, Ph—H), 7.4–7.6 (m, 9H, benzoic-3H, -4H, and -5H), 8.1 (dd, J=8 and 2Hz, 6H, benzoic-2H and -6H), 11.0 (s, 3H, COOH).

EXAMPLE 10

8-[4-[4-(p-Fluorobenzyl)-1-piperidinyl]butyl]-8-azaspiro[4,5] decane-7,9-dione hydrochloride From 4-(p-fluorobenzyl)piperidine (5.1 g, 26.9 mmol), 8-(4-bromobutyl)-8-azaspiro[4,5]decane-7,9-dione (8 g, 26.4 mmol), potassium carbonate (3.6 g, 26.4 mmol) and potassium iodide (0.5 g, 3 mmol) and operating as described in Ex. 9, an oil is obtained which is dissolved in Et$_2$O and precipitated by addition of HCl ethereal solution. The precipitate recrystallizes from isopropanol giving 4.93 g (41%). mp: 192°–194° C.

Analysis elemental for C$_{25}$H$_{35}$N$_2$O$_2$F.HCl (%): (calculated) C 66.58 H 8.05 N 6.21; (found) C 66.37 H 8.10 N 6.00.

IR (cm$^{-1}$): 3200–3700, 2300–2800, 1730, 1675.

NMR (CD$_3$OD): 1.4–2.0 (m, 17H), 2.55–2.7 (s.a., 2H, CH$_2$Ph), 2.65 (s, 4H, CH$_2$CO), 2.85–3.25 (m, 4H, piperidine 2-H$_{ax}$, and 6-H$_{ax}$, and butyl-4H), 3.47 (t.a., J=12Hz, 2H, piperidine 2-H$_{eq}$ and 6-H$_{eq}$), 3.78 (t, J=6,5Hz, 2H, butyl- 1H), 6.98 (t, J=9Hz, 2H, Ph-3H and -5H), 7.20 (dd, J=9 and 6Hz, 2H, Ph-2H and -6H).

EXAMPLE 11

4-(p-Fluorobenzyl)-1-[3-(p-fluorophenoxy)propyl]-piperidine hydrochloride

To the reaction crude oil obtained in Ex. 8, 30 ml of CO$_3$HNa saturated solution are added and then removed with three 15-ml portions of ether. The organic extracts are dried over anhydrous sodium sulfate and evaporated. The residue is redissolved in 45 ml of a mixture of isopropanol-ether (2:8) and precipitated by addition of an ethereal HCl solution. The precipitate is filtered, washed with ether and dried in vacuo giving 3.53 g. mp: 143°–146.5° C.

Elemental analysis for C$_{21}$H$_{25}$F$_2$NO.HCl (%): (calculated) C 66.05 H 6.86 N 3.67 Cl 9.28; (found) C 65.80 H 6.89 N 3.94 Cl 9.46.

IR (KBr) cm$^{-1}$: 3200–3600, 2300–2900, 1520, 1230.

NMR (CDCl$_3$): 1.6–1.8 (m, 5H), 2.1–2.5 (m, 4H), 2.5–2.6 (m, 2H), 3.1 (m, 2H), 3.65 (da, J=12Hz, 2H), 4.0 (t, J=6Hz, 2H), 6.7–7.1 (m, 4H), 7.4–7.5 (m, 2H), 8.1 (dd, J=7 and 3Hz, 2H).

What is claimed is:

1. A 4-benzylpiperidine derivative of the general formula (I):

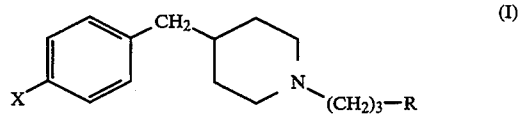

or a pharmaceutically acceptable acid addition salt thereof, wherein X is hydrogen or fluorine and R is hydrogen, or a group selected from p- fluorobenzoyl, α-hydroxy-p-fluorobenzyl, p-fluorophenoxy, bis(p-fluorophenyl)methyl and 8-azaspiro[4,5] decane-7,9-dione-8-yl-methyl, with the proviso that X and R may not be simultaneously hydrogen and p-fluorobenzoyl respectively.

2. The compound of claim 1, wherein said compound is 4-p-Fluorobenzyl-1-propylpiperidine hydrochloride.

3. The compound of claim 1, wherein said compound is 4-p-Fluorobenzyl-1-(4-fluorophenyl-4-oxo)butyl-piperidine hydrochloride.

4. The compound of claim 1, wherein said compound is 4-Benzyl-1-(4-hydroxi-4-p-fluorophenyl)butylpiperidine hydrochloride.

5. The compound of claim 1, wherein said compound is 4-(p-Fluorobenzyl)-1-(4-fluorophenyl-4-hydroxy)butyl piperidine hydrochloride.

6. The compound of claim 1, wherein said compound is 4-(p-Fluorobenzyl)-1-[3-(p-fluorophenoxy)propyl]-piperidine dibenzoate.

7. The compound of claim 1, wherein said compound is 4-(p-Fluorobenzyl)-1-[4,4-bis(p-fluorophenyl)butyl]-piperidine tribenzoate.

8. The compound of claim 1, wherein said compound is 8-[4-[4-(Fluorobenzyl)-1-piperidinyl]butyl]-8-azaspiro [4,5]decane-7,9-dione hydrochloride.

9. The compound of claim 1, wherein said compound is 4-(p-Fluorobenzyl)-1-[3-(p-fluorophenoxy)propyl]-piperidine hydrochloride.

10. A method of treating psychosis comprising administering to a person in need of such treatment an anti-psychotic effective amount of any compound of claim 1.

* * * * *

UNITED STATES PATENT AND TRADEMARK OFFICE
CERTIFICATE OF CORRECTION

PATENT NO. : 5 395 841
DATED : March 7 1995
INVENTOR(S) : FOGUET R. et al.

It is certified that error appears in the above-indentified patent and that said Letters Patent is hereby corrected as shown below:

ON THE COVER:

In Section [54], line 2, please change "PHYCHOSIS" to read --PSYCHOSIS--.

Signed and Sealed this

Twenty-fifth Day of July, 1995

*Attest:*

BRUCE LEHMAN

*Attesting Officer*   *Commissioner of Patents and Trademarks*